US010987007B2

(12) United States Patent
Rundo et al.

(10) Patent No.: US 10,987,007 B2
(45) Date of Patent: Apr. 27, 2021

(54) METHOD OF PROCESSING ELECTROPHYSIOLOGICAL SIGNALS AND CORRESPONDING SYSTEM, VEHICLE, AND COMPUTER PROGRAM PRODUCT

(71) Applicant: STMicroelectronics S.r.l., Agrate Brianza (IT)

(72) Inventors: Francesco Rundo, Gravina di Catania (IT); Sabrina Conoci, Tremestieri Etneo (IT); Piero Fallica, Catania (IT)

(73) Assignee: STMicroelectronics S.R.L., Agrate Brianza (IT)

( * ) Notice: Subject to any disclaimer, the term of this patent is extended or adjusted under 35 U.S.C. 154(b) by 170 days.

(21) Appl. No.: 16/167,817

(22) Filed: Oct. 23, 2018

(65) Prior Publication Data

US 2019/0117096 A1    Apr. 25, 2019

(30) Foreign Application Priority Data

Oct. 24, 2017    (IT) .................. 102017000120714

(51) Int. Cl.
*A61B 5/02* (2006.01)
*A61B 5/024* (2006.01)
(Continued)

(52) U.S. Cl.
CPC ...... *A61B 5/02405* (2013.01); *A61B 5/02416* (2013.01); *A61B 5/04017* (2013.01);
(Continued)

(58) Field of Classification Search
CPC . A61B 5/02405; A61B 5/681; A61B 5/02416; A61B 5/04017; A61B 5/04028;
(Continued)

(56) References Cited

U.S. PATENT DOCUMENTS

| 9,019,666 B2 | 4/2015 | Bourgeat et al. |
| 2014/0066785 A1 | 3/2014 | Watson et al. |

(Continued)

FOREIGN PATENT DOCUMENTS

| WO | 2011089179 A1 | 7/2011 |
| WO | 2017089921 A1 | 6/2017 |

OTHER PUBLICATIONS

Zhu-Cheng et al. "ECG Reconstruction via PPG: A Pilot Study." cyclearXiv:1904.10481v1 [eess.SP] Apr. 23, 2019, pp. 1-4 (Year: 2019).*

(Continued)

*Primary Examiner* — Amanda K Hulbert
(74) *Attorney, Agent, or Firm* — Slater Matsil, LLP

(57) ABSTRACT

A method of processing electrophysiological signals includes: receiving, over a limited time duration, sample electrocardiography (ECG) signals indicative of heart pulsatile activity occurring with a variable heart rate, wherein receiving the sample ECG signals is discontinued at an expiry of the limited time duration; receiving photoplethysmography (PPG) signals indicative of the heart pulsatile activity; determining a correlation between the sample ECG signals and the PPG signals; determining reconstructed ECG signals from the PPG signals as a function of the correlation between the sample ECG signals and the PPG signals; and estimating a heart rate variability of the variable heart rate as a function of the reconstructed ECG signals.

20 Claims, 5 Drawing Sheets

(51) Int. Cl.
*A61B 5/04* (2006.01)
*B60W 40/08* (2012.01)
*G16H 50/30* (2018.01)
*A61B 5/00* (2006.01)
*A61B 5/0402* (2006.01)

(52) U.S. Cl.
CPC ........ *A61B 5/04028* (2013.01); *A61B 5/7278* (2013.01); *B60W 40/08* (2013.01); *G16H 50/30* (2018.01); *A61B 5/7264* (2013.01); *B60W 2040/0872* (2013.01)

(58) Field of Classification Search
CPC ............... A61B 5/7264; A61B 5/7278; B60W 2040/0827; B60W 2040/0872; B60W 2540/221; B60W 40/08; G16H 50/30
See application file for complete search history.

(56) References Cited

U.S. PATENT DOCUMENTS

| | | | | |
|---|---|---|---|---|
| 2015/0366518 | A1* | 12/2015 | Sampson | A61B 5/0478 600/301 |
| 2016/0071393 | A1* | 3/2016 | Kaplan | A61B 5/74 340/539.12 |
| 2016/0345907 | A1 | 12/2016 | Fung et al. | |
| 2016/0354027 | A1* | 12/2016 | Benson | B60N 2/002 |
| 2017/0172510 | A1 | 6/2017 | Homyk et al. | |
| 2018/0192900 | A1* | 7/2018 | Wei | A61B 5/0225 |

OTHER PUBLICATIONS

Rundo, Francesco et al., "An Advanced Bio-Inspired PhotoPlethysmoGraphy (PPG) and ECG Pattern Recognition System for Medical Assessment," Sensors, vol. 18, 405, Jan. 2018, 22 pages.
Saravanamoorthi, A., et al., "Prediction of Drowsy Fault Using Bio Signals Joint Stachostic FSD (BJSFSD) Algorithm," European Journal of Applied Sciences, 8(4): 193-199, Aug. 2014, 7 pages.
Sari, Nila Novita et al., "A Two-Stage Intelligent Model to Extract Features from PPG for Drowsiness Detection," IEEE International Conference on System Science and Engineering (ICSSE), Jul. 7-9, 2016, pp. 1-2.
Selvaraj, N., et al., "Assessment of heart rate variability derived from finger-tip photoplethysmography as compared to electrocardiography," Journal of Medical Engineering & Technology, Dec. 10, 2008, pp. 479-484.
Shin, Kun-Soo, et al., "An Algorithm for Pattern Recognition of Multichannel ECG Signals," Dept. of Electrical Engineering, Yonsei University, Seoul, Korea, Annual International Conference of the IEEE Engineering in Medicine and Biology Society, vol. 12, No. 2, Nov. 1-4, 1990, 2 pages.
Shin, Heung-Sub et al., "Real Time Car Driver's Condition Monitoring System," Sensors, IEEE, Nov. 1, 2010, pp. 951-954.
Shin, Hangsik et al., "Feasibility study for the non-invasive blood pressure estimation based on ppg morphology: normotensive subject study," Biomedical Engineering OnLine, XP055478171, Jan. 10, 2017, pp. 1-14.
Shorten, G.P., et al., "A Time Domain Based Classifier for ECG Pattern Recognition," 33rd Annual International Conference of the IEEE Engineering in Medicine and Biology Society, Boston, Massachusetts, Aug. 30-Sep. 3, 2011, pp. 4980-4983.
Soltane, Mohamed et al., "Artificial neural networks (ANN) Approach to PPG Signal Classification," International Journal of Computing & Information Sciences, Apr. 2004, vol. 2(1), pp. 58-65.
Takagi, Tomohiro et al., "Fuzzy Identification of Systems and Its Applications to Modeling and Control," IEEE Transactions on Systems, Man, and Cybernetics, vol. SMC-15, No. 1, Jan. / Feb. 1985, pp. 116-132.
Tang, S.K. Deric et al., "PPG Signal Reconstruction using a combination of Discrete Wavelet Transform and Empirical Mode Decomposition," Faculty of Engineering, Computing & Science, Swinburne University of Technology Sarawak Campus, Malaysia, Aug. 15-17, 2016, 4 pages.
Teng, X. F., et al., "Continuous and Noninvasive Estimation of Arterial Blood Pressure Using a Photoplethysmographic Approach," Proceedings of the 25th Annual International Conference of the IEEE EMBS, Cancun, Mexico, Sep. 17-21, 2003, 4 pages.
Trahanias, Panagiotis et al., "Syntactic Pattern Recognition of the ECG," IEEE Transactions on Pattern Analysis and Machine Intelligence, vol. 12, No. 7, Jul. 1990, pp. 648-657.
Tuzcu, Volkan et al., "Dynamic Time Warping as a Novel Tool in Pattern Recognition of ECG Changes in Heart Rhythm Disturbances," IEEE International Conference on Systems, Man and Cybernetics, Oct. 12, 2005, pp. 182-186.
Vicente, Jose et al., "Detection of Driver's Drowsiness by Means of HRV Analysis," IEEE Computing in Cardiology, Sep. 18-21, 2011, 38, pp. 89-92.
Vinciguerra, Vincenzo et al., "Progresses towards a Processing Pipeline in Photoplethysmogram (PPG) based on SiPMs," IEEE Proceedings of 23 European Conference on Circuit Theory and Design, Catania (Italy), Sep. 4-6, 2017, 5 pages.
Wu, Chih-Chin et al., "A Wireless Photoplethysmography Signal Processing System for Long-term Monitoring," IEEE International Conference on Consumer Electronics (ICCE), Mar. 14, 2016, 4 pages.
Yadhuraj, S. R., et al., "GUI Creation for Removal of Motion Artifact in PPG Signals," 3rd International Conference on Advanced Computing and Communication Systems (ICACCS—2016), Coimbatore, India, Jan. 22-23, 2016, 5 pages.
Yan, Y. S., et al., "Noninvasive Estimation of Blood Pressure Using Photoplethysmographic Signals in the Period Domain," IEEE Engineering in Medicine and Biology 27th Annual Conference, Sep. 1-4, 2005, pp. 3583-3584.
Yeh, Ming-Feng et al., "ECG signal pattern recognition using grey relational analysis," IEEE International Conference on Networking, Sensing and Control, Mar. 21-23, 2004, Taipei, Taiwan, pp. 725-730.
Yoon, Youngzoon et al., "Nonconstrained Blood Pressure Measurement by Photoplethysmography," Journal of the Optical Society of Korea, vol. 10, No. 2, Jun. 2006, pp. 91-95.
Fletcher, R. et al., "Function minimization by conjugate gradients," The Computing Journal, vol. 7, Issue 2, Jan. 1, 1964 pp. 149-154.
Abe, Erika et al., "Development of Drowsy Driving Accident Prediction by Heart Rate Variability Analysis", IEEE APSIPA, Dec. 9-12, 2014, 4 pages.
Agro, D., et al., "PPG Embedded System for Blood Pressure Monitoring," IEEE AEIT Annual Conference—From Research to Industry: The Need for a More Effective Technology Transfer (AEIT), Trieste, Italy, Sep. 18-19, 2014, 6 pages.
Ali Hassan, M. K., et al., "Measuring Blood Pressure Using a Photoplethysmography Approach," 4th Kuala Lumpur International Conference on Biomedical Engineering, Jan. 2008, 5 pages.
Allen, John, "Photoplethysmography and its application in clinical physiological measurement," IOP Publishing, Physiological Measurement, vol. 28, R1-R39, Topical Review, doi: 10.1088/0967-3334/28/3/R01, Mar. 2007, pp. R1-R39.
Arena, Paolo et al., "Chaos control by using Motor Maps", Chaos Journal, vol. 12, No. 3, Sep. 2002, pp. 559-573.
Arena, Paolo et al., "A CNN-Based Chip for Robot Locomotion Control," IEEE Transactions on Circuits and Systems—I: Regular Papers, vol. 52, No. 9, Sep. 2005, pp. 1862-1871.
Arzi, M., "New Algorithms for Continuous Analysis of Long Term ECG Recordings Using Symplectic Geometry and Fuzzy Pattern Recognition," Computers in Cardiology, Sep. 25-28, 2005, pp. 739-742.
Banerjee, Rohan et al., "Estimation of ECG parameters using photoplethysmography;" 13th IEEE International Conference on BioInformatics and BioEngineering, Nov. 10-13, 2013, pp. 1-5.
Barbe, Kurt et al., "Analyzing the Windkessel Model as a Potential Candidate for Correcting Oscillometric Blood-Pressure Measure-

(56) References Cited

OTHER PUBLICATIONS ments," IEEE Transactions on Instrumentation and Measurement, vol. 61, No. 2, Feb. 2012, pp. 411-418.
Battiato, S., et al., "ALZ: Adaptive Learning for Zooming Digital Images," IEEE International Conference on Consumer Electronics, ICCE 2007. Digest of Technical Papers, Jan. 10-14, 2007, 2 pages.
Bolanos, M., et al., "Comparison of Heart Rate Variability Signal Features Derived from Electrocardiography and Photoplethysmography in Healthy Individuals," IEEE Proceedings of the 28th EMBS Annual International Conference, Engineering in Medicine and Biology Society, New York City, Aug. 30-Sep. 3, 2006, pp. 4289-4294.
Cattivelli, Federico S., et al., "Noninvasive Cuffless Estimation of Blood Pressure from Pulse Arrival Time and Heart Rate with Adaptive Calibration," Sixth International Workshop on Wearable and Implantable Body Sensor Networks, Jun. 3-5, 2009, 6 pages.
Datta, Shreyasi et al., "Blood Pressure Estimation from Photoplethysmogram using Latent Parameters," 2016 IEEE International Conference on Communications (ICC), May 22-27, 2016, 7 pages.
Dutt, D. Narayana et al., "Digital Processing of ECG and PPG Signals for Study of Arterial Parameters for Cardiovascular Risk Assessment," IEEE Communications and Signal Processing (ICCSP), Apr. 2-4, 2015, pp. 1506-1510.
Eftestol, Trygve et al., "A Flexible Pattern Recognition System for Analysis of ECG and Related Demographics and Annotations," Proceedings of the 20th Annual International Conference of the IEEE Engineering in Medicine and Biology Society, vol. 20, No. 1, Biomedical Engineering, Nov. 1, 1998, pp. 135-138.
Elgendi, Mohamed "On the Analysis of Fingertip Photoplethysmogram Signals," Current Cardiology Reviews, vol. 8, Feb. 2012, pp. 14-25.
Ferdinando, Hany et al., "Comparing Features from ECG Pattern and HRV Analysis for Emotion Recognition System," IEEE Conference on Computational Intelligence in Bioinformatics and Computational Biology, Oct. 5-7, 2016, 6 pages.
Fortino, Giancarlo et al., "PPG-based Methods for Non Invasive and Continuous Blood Pressure Measurement: an Overview and Development Issues in Body Sensor Networks," IEEE International Workshop on Medical Measurements and Applications, Apr. 30-May 1, 2010, 4 pages.
Gaurav, Aman et al., "Cuff-Less PPG based Continuous Blood Pressure Monitoring—A Smartphone based Approach," 38th Annual International Conference of the IEEE Engineering in Medicine and Biology Society (EMBC), Aug. 16-20, 2016, 4 pages.
Goldberger, Ary L., et al., "PhysioBank, PhysioToolkit, and PhysioNet Components of a New Research for Complex Physiologic Signals," American Heart Association, Inc., Circulation, Jun. 13, 2000; 101(23): E215-20, 7 pages.
Gu, W. B., et al., "A Novel Parameter from PPG Dicrotic Notch for Estimation of Systolic Blood Pressure Using Pulse Transit Time," Proceedings of the 5th International Workshop on Wearable and Implantable Body Sensor Networks, in conjunction with the 5th International Summer School and Symposium on Medical Devices and Biosensors, Chinese University of Hong Kong, HKSAR, China, Jun. 1-3, 2008, 3 pages.
Hagan, Martin T., et al., "Training Feedforward Networks with the Marquardt Algorithm," IEEE Transactions on Neural Network, Nov. 1994; vol. 5, No. 6, pp. 989-993.
He, Lin et al., "Recognition of ECG Patterns Using Artificial Neural Network," Sixth International Conference on Intelligent Systems Design and Applications, Oct. 16-18, 2006, 5 pages.
Huang, Yo-Ping et al., "Early Detection of Driver Drowsiness by WPT and FLFNN Models," IEEE International Conference on Systems, Man, and Cybernetics (SMC), Budapest, Hungary, Oct. 9-12, 2016, pp. 000463-000468.
Hwang, Taeho et al., "Driver Drowsiness Detection Using the In-Ear EEG," 38th Annual International Conference of the IEEE Engineering in Medicine and Biology Society (EMBC), Orlando, FL, Aug. 16-20, 2016, pp. 4646-4649.

Jeyhani, Vala et al., "Comparison of HRV Parameters Derived from Photoplethysmography and Electrocardiography Signals," Engineering in Medicine and Biology Society (EMBC), 2015 37th Annual International Conference of the IEEE, Aug. 25-29, 2015, pp. 5952-5955.
Jin, Feiming et al., "The Application of Pattern Recognition Technology in the Diagnosis and Analysis on the Heart Disease: Current Status and Future," May 23-25, 2012, 24th Chinese Control and Decision Conference (CCDC), pp. 1304-1307.
Kao, Young-Hua et al., "A PPG Sensor for Continuous Cuffless Blood Pressure Monitoring with Self-Adaptive Signal Processing," Proceedings of the International Conference on Applied System Innovation (ICASI), IEEE-ICASI, 2017—Meen, Prior & Lam (EDS), May 13-17, 2017, 4 pages.
Kavsaoglu, A. Resit et al., "Feature Extraction for Biometric Recognition with Photoplethysmography Signals," IEEE on Signal Processing and Communications Applications Conference (SIU), Apr. 24-26, 2013, 4 pages.
Kim, Jung Yi et al., "Comparative study on artificial neural network with multiple regressions for continuous estimation of blood pressure," Proceedings of the IEEE, Engineering in Medicine and Biology 27th Annual Conference, Shanghai, China, Sep. 1-4, 2005, 4 pages.
Kurylyak, Yuriy et al., "A Neural Network-based Method for Continuous Blood Pressure Estimation from a PPG Signal," IEEE International Instrumentation and Measurement Technology Conference (12MTC), May 6-9, 2013, pp. 280-283.
Kurylyak, Yuriy et al., "Smartphone-Based Photoplethysmogram Measurement," Department of Electronics, Computer and System Sciences, University of Calabria, Rende-CS, Italy, Jan. 2012, 30 pages.
Lamonaca, F., et al., "Reliable Pulse Rate Evaluation by Smartphone," IEEE International Symposium on Medical Measurements and Applications Proceedings, May 18-19, 2012, 4 pages.
Lawoyin, Samuel, "Novel technologies for the detection and mitigation of drowsy driving," VCU Virginia Commonwealth University, VCU Scholars Compass, Thesis and Dissertations, http://scholarscompass.vcu.edu/etd/3639, Dec. 2014, 320 pages.
Lee, Jaewon et al., "Correlation Analysis between Electrocardiography (ECG) and Photoplethysmogram (PPG) Data for Driver's Drowsiness Detection Using Noise Replacement Method," Procedia Computer Science, vol. 116, Oct. 13-14, 2017, pp. 421-426, ISSN 1877-0509.
Li, Gang et al., "Detection of Driver Drowsiness Using Wavelet Analysis of Heart Rate Variability and a Support Vector Machine Classifier," Sensors (Basel, Switzerland), Dec. 2013(13), www.mdpi.com/journal/sensors, pp. 16494-16511.
Liao, Jia-Ju et al., "An Effective Photoplethysomgraphy Signal Processing System Based on EEMD Method," Department of Electronics Engineering, National Chiao Tung University, Apr. 27-29, 2015, 4 pages.
Liu, Mengyang et al., "Cuffless Blood Pressure Estimation Based on Photoplethysmography Signal and Its Second Derivative," International Journal of Computer Theory and Engineering, vol. 9, No. 3, XP055478166, Jun. 2017, pp. 202-206.
Lu, Guohua et al., "A comparison of photoplethysmography and ECG recording to analyse heart rate variability in healthy subjects," Journal of Medical Engineering & Technology, vol. 33, ISSN: 0309-1902, Dec. 15, 2009, pp. 634-641.
Madhav, K. Venu et al., "Estimation of Respiration Rate from ECG, BP and PPG signals using Empirical Mode Decomposition," IEEE International Instrumentation and Measurement Technology Conference, May 10-12, 2011, pp. 1-4.
Mazomenos, E. B., "A Time-Domain Morphology and Gradient based Algorithm for ECG Feature Extraction," IEEE International Conference on Industrial Technology (ICIT), Mar. 19-21, 2012, pp. 117-122.
Mazzillo, Massimo et al., "Electro-Optical Pof p-on-n and n-on-p Silicon Photomultipliers," IEEE Trans. Electron Devices, vol. 59, No. 12, Dec. 2012, pp. 3419-3425.
Mazzillo, Massimo et al., "Silicon Photomultiplier Technology at STMicroelectronics", IEEE Transactions on Nuclear Science, vol. 56, No. 4, Aug. 2009, 9 pages.

(56) References Cited

OTHER PUBLICATIONS

McCombie, Devin B., et al., "Adaptive blood pressure estimation from wearable PPG sensors using peripheral artery pulse wave velocity measurements and multi-channel blind identification of local arterial dynamics," Proceedings of the 28th IEEE, EMBS Annual International Conference, New York City, NY, USA, Aug. 30-Sep. 3, 2006, 4 pages.

Meigas, Kalju et al., "Continuous Blood Pressure Monitoring Using Pulse Wave Delay," IEEE Proceedings of the 23rd Annual EMBS International Conference, Oct. 25-28, 2001, Istanbul, Turkey, pp. 3171-3174.

Oreggia, D., et al., "Physiological parameters measurements in a cardiac cycle via a combo PPG-ECG system," Department of Energy, Information Engineering and Mathematical Models (DEIM)—University of Palermo, IMS R&D, STMicroelectronics, Oct. 14-16, 2015, 6 pages.

Page, Adam et al., "Utilizing Deep Neural Nets for an Embedded ECG-based Biometric Authentication System," Oct. 22-24, 2015 IEEE Biomedical Circuits and Systems Conference (BioCAS), pp. 1-4.

Peng, Fulai et al., "Motion artifact removal from photoplethysmographic signals by combining temporally constrained independent component analysis and adaptive filter," BioMedical Engineering OnLine, Apr. 24, 2017, 14 pages.

Raghuram, M., et al., "Use of Complex EMD generated Noise Reference for Adaptive reduction of Motion Artifacts from PPG Signals," Dept. of E&I Eng., Kakatiya Institute of Technology & Science, Dept. of ECE, Talla Padmavathi College of Engineering, Kazipet, International Conference on Electrical, Electronics, and Optimization Techniques (ICEEOT), Mar. 3-5, 2016, 5 pages.

Rundo, Francesco et al., "An Innovative Reaction-Diffusion Bio-Inspired Pipeline for Physiological Signals Analysis," ResearchGate, Conference Paper 2017, STMicroelectronics, Catania Italy, Oct. 2017, 2 pages.

\* cited by examiner

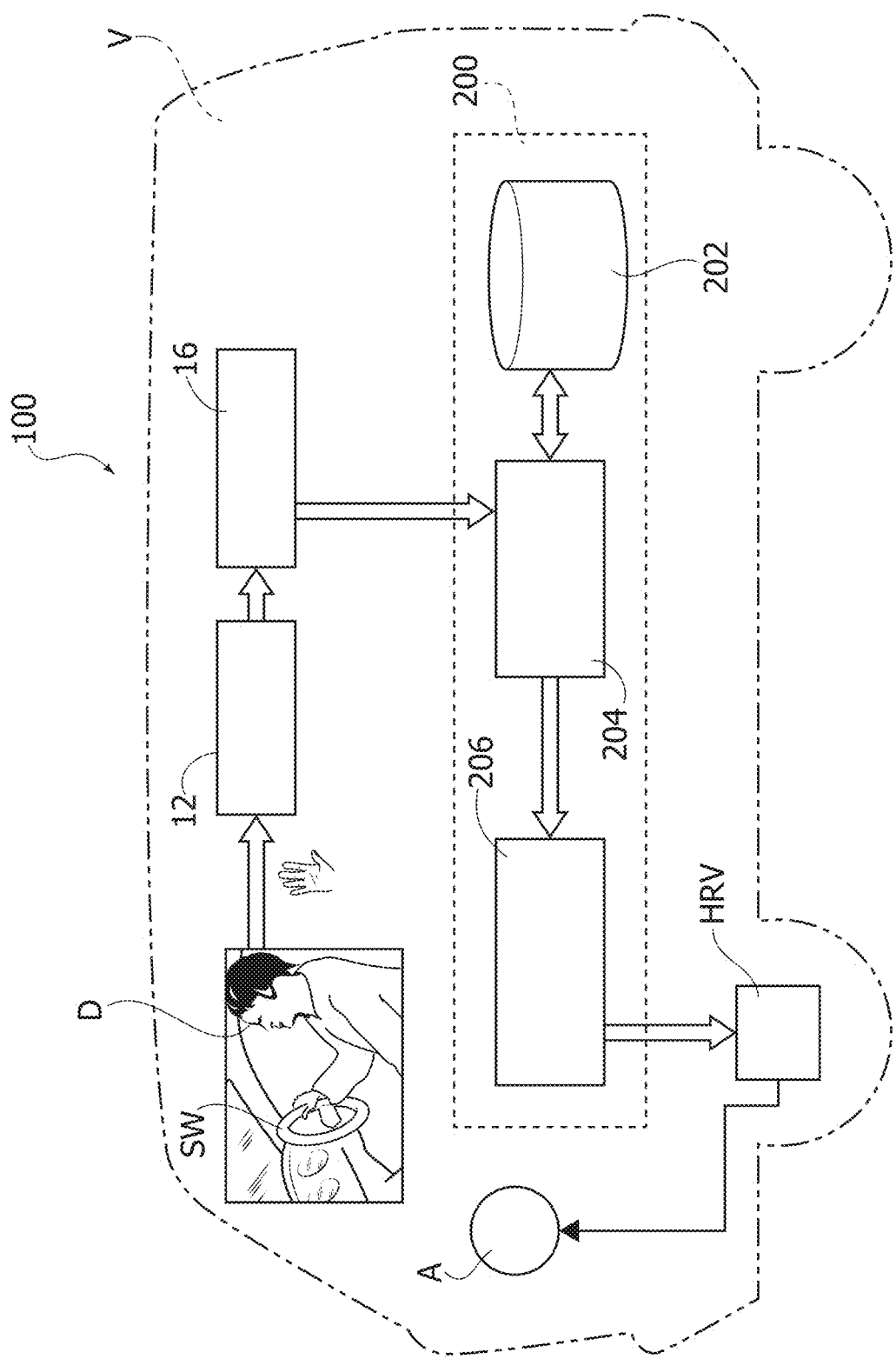

METHOD OF PROCESSING ELECTROPHYSIOLOGICAL SIGNALS AND CORRESPONDING SYSTEM, VEHICLE, AND COMPUTER PROGRAM PRODUCT

CROSS-REFERENCE TO RELATED APPLICATIONS

This application claims priority to Italian Patent Application No. 102017000120714, filed on Oct. 24, 2017, which application is hereby incorporated herein by reference.

TECHNICAL FIELD

The description relates to processing electrophysiological signals and, in particular embodiments, to a method of processing electrophysiological signals, and a corresponding system, vehicle, and computer program product.

BACKGROUND

Drowsiness of a vehicle driver (e.g. before and during driving) may adversely affect driving safety. This appears to be particularly the case with long-haul commercial vehicles such as trucks or buses, whose drivers are oftentimes forced to drive for long time spans, even at night, without breaks.

A correlation is known to exist between drowsiness and heart rate variability (HRV), so that estimating HRV of a driver may permit to obtain useful information concerning possible drowsiness.

A conventional way of computing a HRV signal involves processing a robust and effective electrocardiography (ECG) time series.

A basic issue in that respect lies in that such an ECG signal cannot be easily detected on board a vehicle, for example because multiple detection points (at least two) are involved in sampling an ECG signal.

At least in principle, installing ECG detectors on the car steering wheel of a vehicle could be contemplated. Satisfactory operation would however require that both the driver's hands should be steadily placed on the car steering wheel at those positions where the ECG detectors are located. This is however a highly unrealistic scenario.

SUMMARY

An object of one or more embodiments is to contribute in addressing those issues, thus making it possible to obtaining a reliable estimate of HRV from which a possible condition of drowsiness can be detected.

One or more embodiments may relate to a corresponding system as well as to a vehicle (e.g. a motor vehicle such as a motor car, a truck, a bus) equipped with such as system.

One or more embodiments may include a computer program product loadable in the memory of at least one processing circuit (e.g., a computer) and including software code portions for executing the steps of the method when the product is run on at least one processing circuit. As used herein, reference to such a computer program product is understood as being equivalent to reference to a non-transitory computer-readable medium containing instructions for controlling the processing system in order to co-ordinate implementation of the method according to one or more embodiments. Reference to "at least one computer" is intended to highlight the possibility for one or more embodiments to be implemented in modular and/or distributed form.

One or more embodiments may provide a pipeline for reconstructing a driver's ECG signal from corresponding PPG signals, that is signals obtained via photoplethysmography. These signals can be sampled on board a vehicle e.g. coupled LEDs-SiPM sensor devices (or any sensor device suited for that purpose), which can be installed in a steering wheel of a vehicle.

One or more embodiments may dispense with the need of having both driver hands on the car steering wheel by resorting to e.g. two electrical detectors installed on the steering wheel activated for a limited time-range ECG sampling (40/50 sec without overlap); after such limited-time ECG sampling, the electrical detectors can be switched off, with an ensuing reduction of power consumption and with PPG signals provided by detectors installed at the vehicle steering wheel.

In one or more embodiments, a neural network, e.g. a self-organizing system (NSOS) supplied with PPG signals obtained from PPG sensors installed in or at the steering wheel will be able to define a correlation between sampled ECG and PPG signals, with the ability of reconstructing an ECG signal for use in HRV estimation even if the driver has not both hands on the car steering wheel (or ECG detectors provided thereon).

In one or more embodiments, a check can by performed time-by-time as to the correlation of ECG and PPG signals obtained for the driver, with the possibility of, e.g., performing re-training the system to take into account possible changes, e.g., in the input PPG dynamics due to the presence of a different driver.

One or more embodiments may provide the functions exemplified above with good precision and reduced computational cost.

One or more embodiments may provide one or more of the following advantages: drowsiness detection based on HRV made possible without the continuous provision of ECG signals; easy detection via PPG signals obtained via probes at a vehicle steering wheel, possibly with only one detection point; ability to learn cross-correlation between a driver's ECG and PPG signals without continuous learning, e.g. with learning possibly limited to system start-up or to relevant differences detected between stored PPG signals and new ones e.g. due to the presence of a new driver; reduction of power consumption due e.g. the possibility of switching off ECG detector probes after a learning phase; good performance in ECG reconstruction, e.g. with high precision in detecting RR intervals in reconstructed ECG signals; and high speed computation due to usage of e.g. LV (Levenberg-Marquardt) and motor map neural network processing suited to be implemented also with analog electronics.

BRIEF DESCRIPTION OF THE DRAWINGS

One or more embodiments will now be described, by way of example only with reference to the annexed figures, wherein:

FIG. 9 is a block diagram exemplary of a possible mode of operation of the pipeline of FIG. 3.

DETAILED DESCRIPTION OF ILLUSTRATIVE EMBODIMENTS

In the ensuing description, one or more specific details are illustrated, aimed at providing an in-depth understanding of examples of embodiments of this description. The embodiments may be obtained without one or more of the specific details, or with other methods, components, materials, etc. In other cases, known structures, materials, or operations are not illustrated or described in detail so that certain aspects of embodiments will not be obscured.

Reference to "an embodiment" or "one embodiment" in the framework of the present description is intended to indicate that a particular configuration, structure, or characteristic described in relation to the embodiment is included in at least one embodiment. Hence, phrases such as "in an embodiment" or "in one embodiment" that may be present in one or more points of the present description do not necessarily refer to one and the same embodiment. Moreover, particular conformations, structures, or characteristics may be combined in any adequate way in one or more embodiments.

The references used herein are provided merely for convenience and hence do not define the extent of protection or the scope of the embodiments.

One or more embodiments may be applied to processing electrophysiological signals such as e.g. electrocardiography (ECG) and photoplethysmography (PPG) signals.

One or more embodiments may be useful in obtaining information from the living body of the driver of a vehicle with a view to possibly generating alert signals and/or activating safety procedures (e.g. taking over control of the vehicle) within the framework of an advanced driver-assistance systems (ADAS).

Electrocardiography (ECG) is the process of recording the electrical activity of the heart over a period of time using electrodes placed on the skin. These electrodes detect the tiny electrical changes on the skin that arise from electrophysiological patterns of de-polarization and re-polarization which occur during each heartbeat of the heart muscle. Electrocardiography is a cardiology test very commonly performed.

Figure 1:
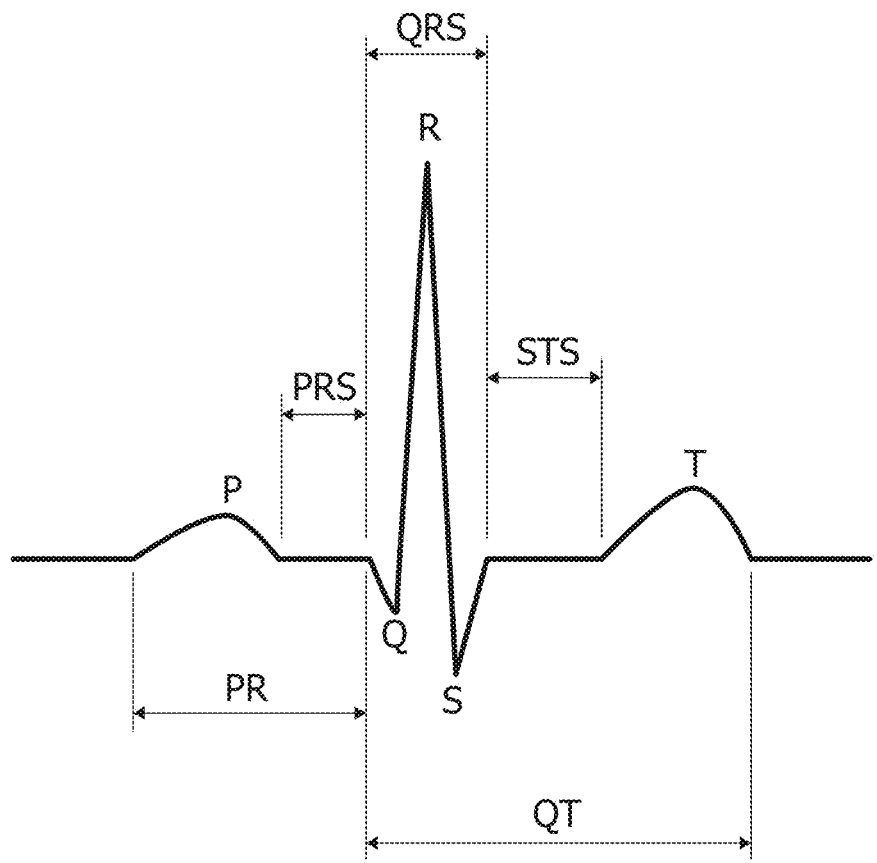
FIGS. 1 and 2 are exemplary of electrocardiography (ECG) and photoplethysmography (PPG) signals.

As schematically exemplified in FIG. 1, and according to a conventional representation, a typical ECG waveform includes two intervals: a PR interval, including a P waveform and a so-called PR segment PRS; and a QT interval, in turn including Q, R, S waveforms (QRS complex), a ST segment STS and a T waveform.

Photoplethysmography (PPG) is a simple and low-cost optical technique that can be used to detect blood volume changes in the microvascular bed of tissue. It is often used non-invasively to make measurements at the skin surface. The PPG waveform includes a pulsatile ('AC') physiological waveform attributed to cardiac synchronous changes in the blood volume with each heartbeat, and is superimposed on a slowly varying ('DC') baseline with various lower frequency components attributed to respiration, thermoregulation, skin tissues, etc. For each cardiac cycle the heart pumps blood to the periphery. Even though this pressure pulse is somewhat dampened by the time it reaches the skin, it is enough to distend the arteries and arterioles in the subcutaneous tissue. If a light reflex/transmit detector device is attached over the skin, a pressure pulse can also be seen from the venous plexus, as a small secondary peak. The change in volume caused by the pressure pulse is detected by illuminating the skin with the light from a light-emitting diode (LED) and then measuring the amount of light either transmitted or reflected to a photodiode. Each cardiac cycle appears as a peak. Because blood flow to the skin can be modulated by multiple other physiological systems, PPG can also be used to monitor breathing, hypovolemia, circulatory conditions as well as for subjective analysis. Additionally, the shape of the PPG waveform differs from subject to subject, and varies with the location and manner in which the pulse oximeter is attached.

Figure 2:
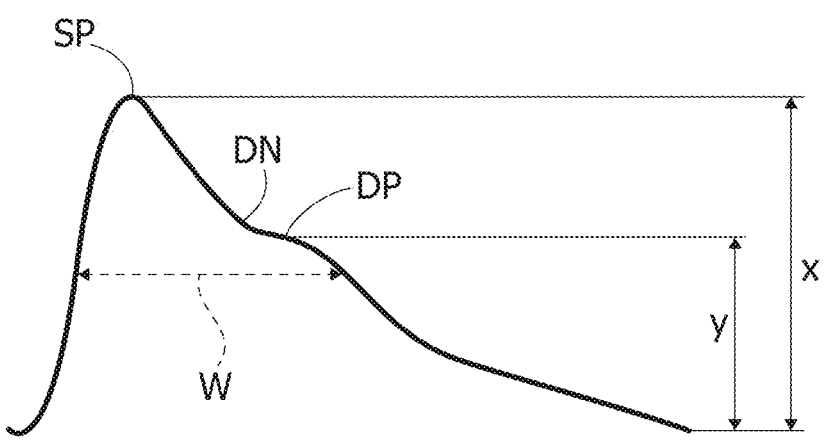

As schematically exemplified in FIG. 2, and again according to a conventional representation, a typical PPG waveform includes: a systolic peak SP at a peak value x; a dicrotic notch DN; and a distolic peak DP at a value y.

A width W of the pulse may also be defined at a given value of the PPG value.

PPG signals can be detected by using detection devices including LED emitters operating at specific wavelengths (usually infrared at 940 nm) and SiPM photomultipliers.

Light emitted by the LEDs is absorbed by the skin (DC component) and the arteries, specifically, by oxygenated (and partly by de-oxygenated) hemoglobin (AC component).

Residual propagated/reflected (e.g. back-scattered) light can be a function (proportional-differential) to the amount of light absorbed by blood hemoglobin in the various heart phases (systolic, diastolic, dicrotic, etc . . . ). A photomultiplier (e.g. a silicon photomultiplier SiPM) may thus detect the presence of photons in the propagated/reflected light by transducing an electrical signal that can be sampled by an e.g. 24-bit ADC thus providing PPG signal as discussed previously.

Various studies have demonstrated the possibility or reconstructing the state of attention of an individual (such as the driver of a motor vehicle) by analyzing heart rate variability—HRV, possibly as derived from studying ECG signals (e.g. by calculating the spectral density of the RR dynamics).

Documents exemplary of such investigations include, e.g.: J. Vicente et al.: "Detection of Driver's Drowsiness by Means of HRV Analysis", IEEE Computing in Cardiology, 2011; 38: 89-92; and E. Abe et al.: "Development of Drowsy Driving Accident Prediction by Heart Rate Variability Analysis", IEEE APSIPA, 2014.

Various other documents are otherwise exemplary of advances in respect of the possibility of exploiting relationships between ECG, PPG, and HRV signal for of estimating various physiological parameters, e.g.: R. Banerjee, et al., "Estimation of ECG parameters using photoplethysmography", 13th IEEE International Conference on BioInformatics and BioEngineering; Year: 2013, pp. 1-5; V. Jeyhani, et al., "Comparison of HRV parameters derived from photoplethysmography and electrocardiography signals", 2015 37th Annual International Conference of the IEEE Engineering in Medicine and Biology Society (EMBC); Year: 2015, pp. 5952-5955; K. Venu Madhav, et al., "Estimation of respiration rate from ECG, BP and PPG signals using empirical mode decomposition", 2011 IEEE International Instrumentation and Measurement Technology Conference; Year: 2011, pp. 1-4; M. Bolanos, et al., "Comparison of heart rate variability signal features derived from electrocardiography and photoplethysmography in healthy individuals", Proc. 28th Annual Int. Conf. of the IEEE EMBS, New York City, USA, 2006; N. Selvaraj, et al., "Assessment of heart rate variability derived from finger-tip photoplethysmography as compared to electrocardiography", Journal of Medical Engineering & Technology 2008, pp. 479484; Elgendi M., "On the analysis of fingertip photoplethysmogram signals", Current Cardiology Reviews, Vol. 8, 2012, pp. 14-25; and Mazomenos, E. B., "A Time-Domain Morphology and Gradient based Igorithm for ECG Feature Extraction", in: Proc: International Conference on Industrial Technology (ICIT), 2012, pp. 117-122.

The solutions reported in these documents were observed to be affected by various drawbacks, such as e.g.: low precision in ECG reconstruction; inability to follow ECG changing dynamics by using PPG dynamics; long training sessions/extensive training set may be required; time and CPU consuming approaches; computational complexity due to the use of complex classification systems; PPG classification and feature extraction required before ECG reconstruction; and CPU consuming procedures, not suited to be implemented e.g. via high-speed HW solution.

These drawbacks inevitably militate against the possible implementation on board of a motor vehicle (e.g. a motor car) at costs reasonably compatible with large-scale use in the automotive sector.

While the possible link between HRV and drowsiness is known, an issue may lie in that computing HRV is facilitated by the availability of a robust and effective ECG time series. This cannot be easily sampled on board a vehicle even in the presence of multiple (e.g. at least two) detection points on the car steering wheel insofar as this would involve the driver's hands being placed continuously (at fixed locations) on the steering wheel.

Figure 3:
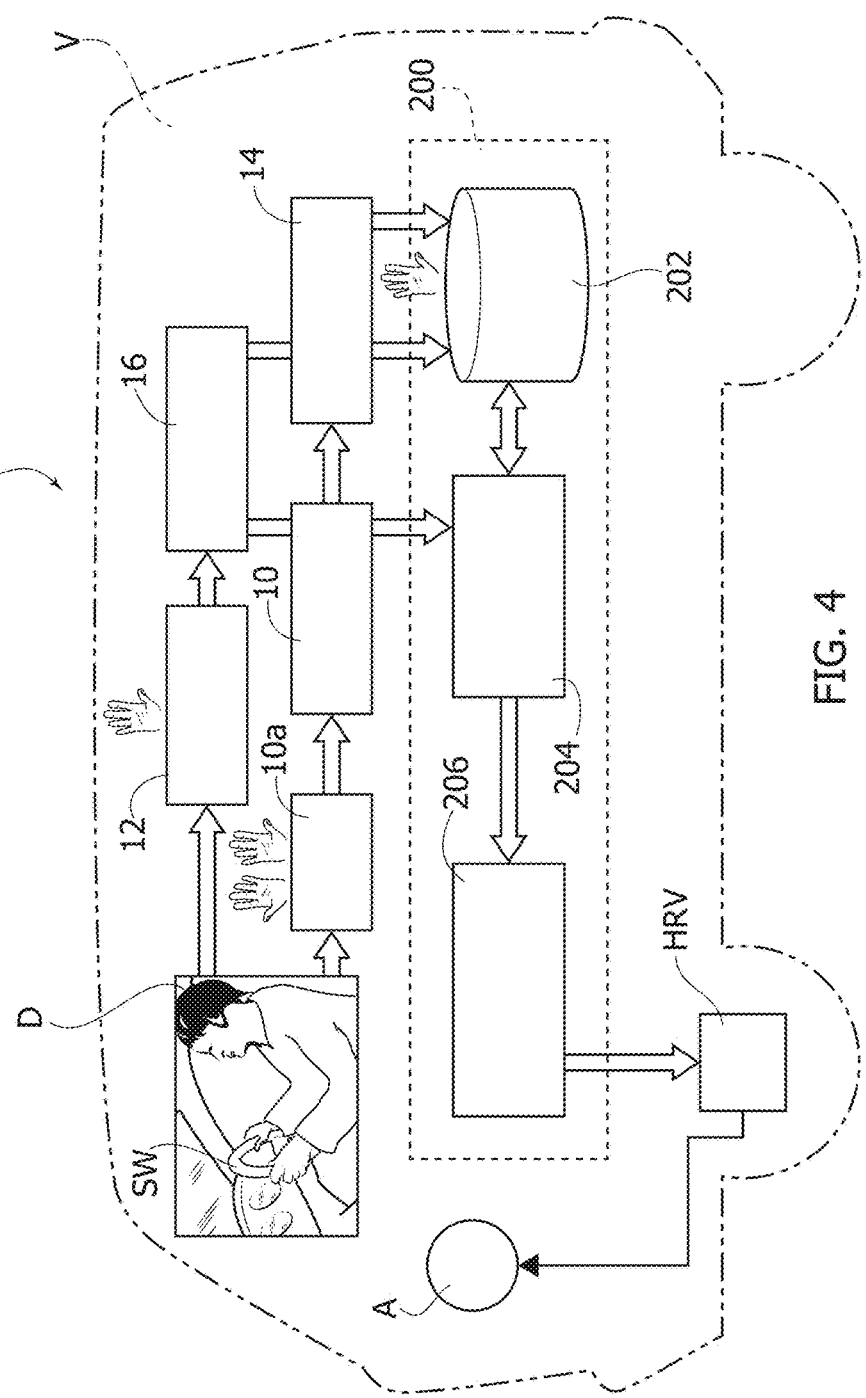
FIG. 3 is a block diagram of a signal processing pipeline in embodiments.

One or more embodiments may provide a system 100 as exemplified in FIG. 3 which is adapted to be installed on board a motor vehicle V (e.g. a motor car) with the capability of obtaining a reliable estimate of HRV from which a possible condition of drowsiness of the driver D can be detected.

In one or more embodiments, the system 100 can be configured for reconstructing robust and effective ECG signals (for use in estimating HRV and thus a possible condition of drowsiness) primarily from PPG signals.

As exemplified in FIG. 3, the system 100 may include plural (e.g. two) electrical detectors 10, of any known type, arranged e.g. at opposed positions on the steering wheel SW of the vehicle V so that they may be "clutched" by the driver D and thus act as ECG sensing probes.

In one or more embodiments, the ECG probes 10 may have associated a timer circuit 10a adapted to activate (automatically or as a result of driver input) the probes and sensing circuitry (of a type known per se) for a limited ECG sampling time (e.g. 40/50 sec without overlap). After such (time limited) ECG sampling, the ECG detectors (probes and associated circuitry) can be switched off, thus reducing power consumption.

In one or more embodiments, ECG sampling (e.g. 40/50 secs) can be performed also discontinuously, so that the whole time range (e.g. 40/50 sec) can be also obtained cumulatively by summing several ECG sub-time-range sampling actions that overall add up to 40/50 sec. That is, in one or more embodiments, the limited time duration over which ECG sampling is performed has a certain cumulative duration, e.g. not in excess of about 50 seconds, preferably between about 40 seconds and 50 seconds.

As exemplified in FIG. 3, the system 100 may further include a set of PPG detectors 12 (infrared LEDs+SiPM detectors) adapted to perform sampling of PPG time series of the driver D from one or both hands placed at the vehicle steering wheel SW.

As noted, used of PPG probes including Silicon Photomultiplier (SiPM) detectors may provide advantages in terms of single-photon sensitivity and high internal gain for relatively low reverse bias. It was observed (see e.g. D. Agrò, et al., "PPG embedded system for blood pressure monitoring," in AEIT Annual Conference—From Research to Industry: The Need for a More Effective Technology Transfer (AEIT), Trieste, 2014), that Silicon PhotoMultipliers (SiPM's) can provide advantages in PPG systems in terms of higher AC-to-DC ratio in PPG pulse waveform, high repeatability and immunity to motion artifacts and ambient interferences. One or more embodiments as discussed herein may sense PPG signals by using SiPMs (as available with companies of the ST group) as optical probe sensors, adapted to be used in conjunction with hardware and software components in providing a signal processing pipeline.

Figure 4:
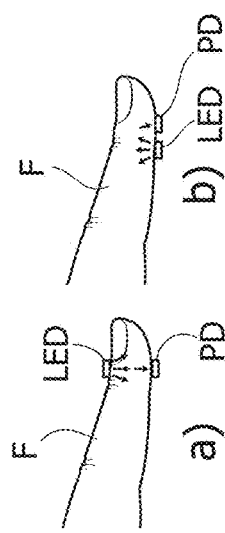
FIG. 4 is exemplary of possible operation of PPG sensors.

One or more embodiments may take advantage of the capability of such PPG probes/detectors of operating both in transmission mode (see e.g. portion (a) in FIG. 4) that is with radiation from the LED propagating through the driver's body, for instance through a fingertip and in reflection mode (see e.g. portion (b) in FIG. 4) that is with radiation from the LED propagating reflected (back-scattered) from the driver's body.

This permits to further relax the requirements for possible positioning of the driver's hands with respect to the PPG sensing action.

One or more embodiments thus address the issues related to discovering possible drowsiness of the driver D (before and during the driving) starting from heart rate variability (HRV) estimation effected reliably on board a vehicle.

In one or more embodiments, the ECG and PPG signals sensed at 10 and 12 (over a limited time span, in the case of the ECG signals), possibly after ECG filtering/pattern recognition at 14 and PPG filtering/pattern recognition at 16 (as discussed in the following), may be fed to a neural self-organizing system (NSOS) 200.

In one or more embodiments, the system 200 can be configured for defining a correlation between the ECG signals sampled over a limited sampling time at 10 and the PPG signal obtained at 12 in order to reconstruct ECG waveforms for use in HRV estimation (and thus in drowsiness detection) even if the driver D has not both hands kept continuously on the car steering wheel SW (or the ECG detectors).

In one or more embodiments, the system 200 can be configured to check, time-by-time, if the PPG signal of the driver is correlated to the sampled ECG, by possibly activating a re-training of the system in the presence of a change in input PPG dynamics (due e.g. to a different driver).

Figure 5:
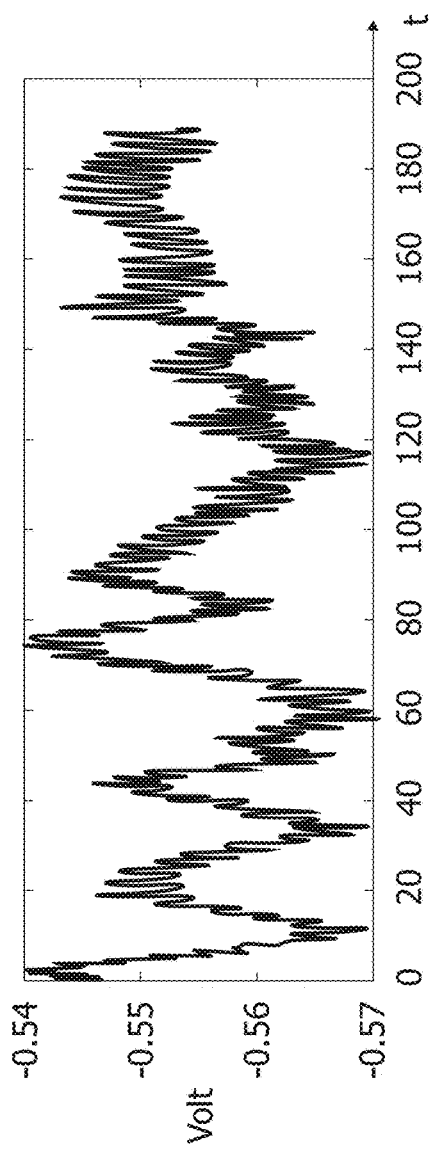
FIGS. 5 and 6 are exemplary of the possible time behavior of PPG signals.
Figure 6:
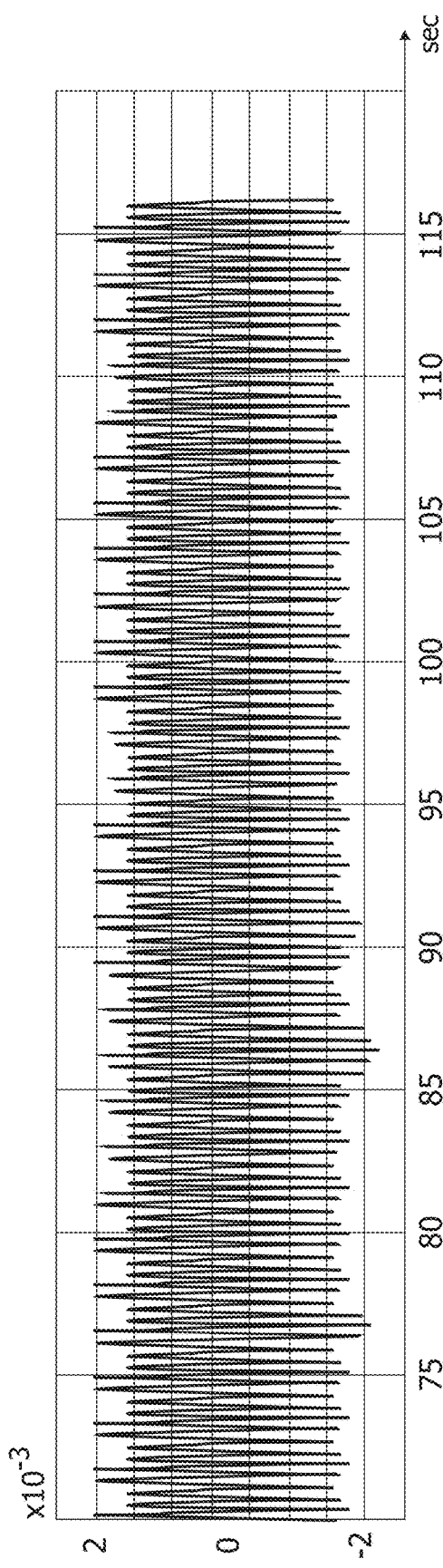

FIGS. 5 and 6 are exemplary of a possible time behavior for "raw" PPG signals as sensed at 12 (FIG. 5) and for "clean" PPG signals as resulting from PPG filtering/pattern recognition at 16.

In one or more embodiments the PPG probe section 12 can be based on the use of large area n-on-p SiPMs fabricated at STMicroelectronics (see e.g. M. Mazzillo, et al., "Silicon Photomultiplier technology at STMicroelectronics", IEEE Trans. Nucl. Sci, vol. 56, no. 4, pp. 2434-2442, 2009). These SiPMs have a total area of 4.0×4.5 mm$^2$ and 4871 square microcells with 60 micron (1 micron=$10^{-6}$ m) pitch. These devices have a geometrical fill factor of 67.4% and are packaged in a surface mount housing (SMD) with 5.1×5.1 mm$^2$ total area (see e.g. M. Mazzillo, et al., cited above or M. Mazzillo, et al., "Electro-optical performances of p-on-n and n-on-p silicon photomultipliers," IEEE Trans. Electron Devices, vol. 59, no. 12, pp. 3419-3425, 2012).

A Pixelteq dichroic bandpass filter with a pass band centered at 542 nm with a Full Width at Half Maximum (FWHM) of 70 nm (1 nm=$10^{-9}$ m) and an optical transmission higher than 90% in the pass band range can be glued on the SMD package by using a Loctite® 352™ adhesive. With the dichroic filter at 3V-0V the SiPM has a maximum detection efficiency of about 29.4% at 565 nm and a PDE of about 27.4% at 540 nm (central wavelength in the filter pass band −1 nm=$10^{-9}$ m). It was noted that the dichroic filter can reduce in excess of 60% the absorption of environmental light in the linear operation range of the detector operating in Geiger mode above its breakdown voltage (~27V). OSRAM LT M673 LEDs in SMD package emitting at 529 nm (1 nm=$10^{-9}$ m) and based on InGaN technology have been used as optical light sources in exemplary embodiments. These LEDs have an area of 2.3×1.5 mm$^2$, viewing angle of 120°, spectral bandwidth of 33 nm (1 nm=$10^{-9}$ m) and typical power emission of a few mW in the standard operation range.

For the purpose of producing "clean" PPG signals as exemplified in FIG. 6, one or more embodiments may adopt (e.g. at 16) the solution described in Italian Patent Application No. 102017000081018 (see corresponding U.S. patent application Ser. No. 16/037,328) and also discussed in: F. Rundo et al., "Progresses towards a Processing Pipeline in Photoplethysmogram (PPG) based on SiPMs", IEEE Proceedings of 23 European Conference on Circuit Theory and Design, Catania (Italy) 4-6 Sep. 2017; F. Rundo et al., "An Advanced Bio-Inspired PhotoPlethysmoGraphy (PPG) and ECG Pattern Recognition System for Medical Assessment." Sensors 2018, 18, 405.

Such a solution makes it possible to correct PPG signal distortion by means of a processing pipeline including a PPG raw signal filter, in turn including an e.g. FIR pass-band scheme (e.g. low-pass plus high-pass), a PPG pattern recognition system as well as a system for detecting and extract medical indicators.

Such a solution can be adapted for use in one or more embodiments e.g. based on the use of: ECG/PPG sensors (e.g. Silicon PhotoMultipliers—SiPM for PPG sensing); a digital filter block for preliminary filtering of ECG/PPG raw signals; a "bio-inspired" PPG Pattern Recognition System—BI-P2RS; a "bio-inspired" ECG Pattern Recognition System—BI-ECG-PR; and facilitated ECG pattern recognition involving mathematical correlation and medical assessment of a segmented ECG waveform (BCG/dPPG/dt/ECG).

The documents cited above also disclose collecting together with the PPG signals a time series of ECG signal waveforms and performing cross-correlation between the ECG signal waveforms and (e.g. the first derivative of) the PPG signals, and validating as valid ECG signal waveforms those ECG signal waveforms which exhibit cross-correlation scores reaching a certain validation threshold.

While a similar approach may facilitate implementing embodiments herein, the embodiments are not by necessity linked to the adoption of the approach discussed in the Rundo et al. documents mentioned above.

In one or more embodiments, the ECG and PPG signals, after possible ECG filtering/pattern recognition at 14 and PPG filtering/pattern recognition at 16, may be fed to a storage 202 in the neural system (NSOS) 200 as well as to a first block 204 which, in one or more embodiments, may include a processing pipeline implementing (in manner known per se) a neural network such as e.g. a Levenberg-Marquardt(LV) Multi-Layer Perceptron Neural Network (LV MLP).

The above-mentioned LV Neural Network is a well-known system described in the literature, e.g. in: Hagan M. T., et al., "Training feed-forward networks with the Marquardt algorithm", IEEE Trans. Neural Netw., 1994; vol. 5, no. 6, pp. 989-993.

Figure 7:
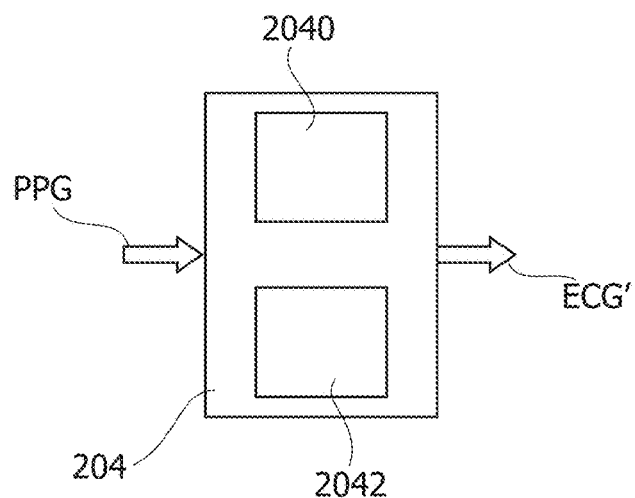
FIGS. 7 and 8 are functional diagram exemplary of possible neural network processing of signals in embodiments.

As exemplified in FIG. 7, in one or more embodiments the circuit block 204 may implement, with the possible support of the storage 202, a neural model (including, in a manner known per se, the creation of a Jacobian matrix 2040 and a gradient step descent procedure 2042), which receives a single PPG waveform as an input and may provide a corresponding ECG waveform as an output.

By means of LV back propagation algorithm (and by rescaling/normalization e.g. as discussed in the Rundo et al. documents mentioned above) the block 204 is able to reconstruct from the PPG signals as sensed at 12, corresponding ECG signals (for use in HRV, and thus drowsiness estimation) even when such signals are not (no longer) obtainable due to the probes 10 being disabled by the timing circuit 10*a*.

The purpose of the block 204 is to train an artificial intelligence system in order that this may learn the correlation between the PPG signal and the ECG signal of a vehicle driver.

A Multi-Layer Perceptron (MLP) feed-forward network (including an input neuron layer, a so-called "hidden" neuron layer and an output neuron layer) and whose training can be based on the Levenberg-Marquardt (LV) algorithm as described by Hagan M. T., et al. in: "Training feed-forward networks with the Marquardt algorithm" (already cited) was found to be adequate for that purpose. The PPG signal (e.g. as processed at 16) can be segmented (for instance by using the techniques described in the Rundo et al. papers cited previously) so that individual PPG waveforms are input to the neural network.

The training set of the LV network can include the various PPG patterns in the (e.g. filtered) PPG signal, possibly formatted and normalized over the [0,1] range.

In one or more embodiments, training of the neural network is of the supervised type. A learning target can thus be provided, e.g. in the form of the result the network is expected to provide if a certain PPG pattern is applied as an input. The target/output set can thus be represented by a corresponding ECG pattern (that is, corresponding to the PPG pattern applied to the input).

In one or more embodiments, the LV learning algorithm (operating in a manner known per se) will enable the network to learn the (non-linear) mathematical model which "maps" the PPG signal (for a certain driver) onto the ECG signal for the same driver.

It is observed that, at least under certain circumstances, such a network may not reconstruct adequately a mathematical model for the PPG to ECG mapping.

Specifically it is found that the block 204 (i.e. the first section in the neural network system 200) may provide a shape correspondence which makes it possible to obtain an ECG signal reconstructed from the PPG which can be superposed in terms of "pattern/shape" over a desired result without however exhibiting a degree of reliability which may permit to use it as a "robust" ECG in producing the HRV evaluation.

Stated otherwise, at least under certain circumstances, the result obtainable from the block 204 may not exhibit precision and robustness as desirable for a ECG signal intended to be used for reconstructing a HRV for drowsiness estimation.

For that reason, in one or more embodiments another neural network 206 of a different type is cascaded to the block 204 in order to complete training and obtain a model which, as a whole, makes it possible to reconstruct an ECG signal robust enough to provide a reliable HRV.

In one or more embodiments, in order to improve ECG reconstruction from the PPG signals, another neural system circuit block 206 may be provided having an input layer 2060 with weights win(x,y,t) to receive as an input the ECG signal (designated ECG') reconstructed from the previous LV neural network 204 and an output layer 2062 with weights wout(x,y,t) to provide a final ECG signal, $ECG^{CMM}$, close(r) to a real ECG.

In one or more embodiments, the block 206 may implement a motor map neural system essentially as described in P. Arena, et al., "Chaos control by using Motor Maps", Chaos Journal, Vol. 12, No. 3, 2002, pp. 559-573.

Figure 8:
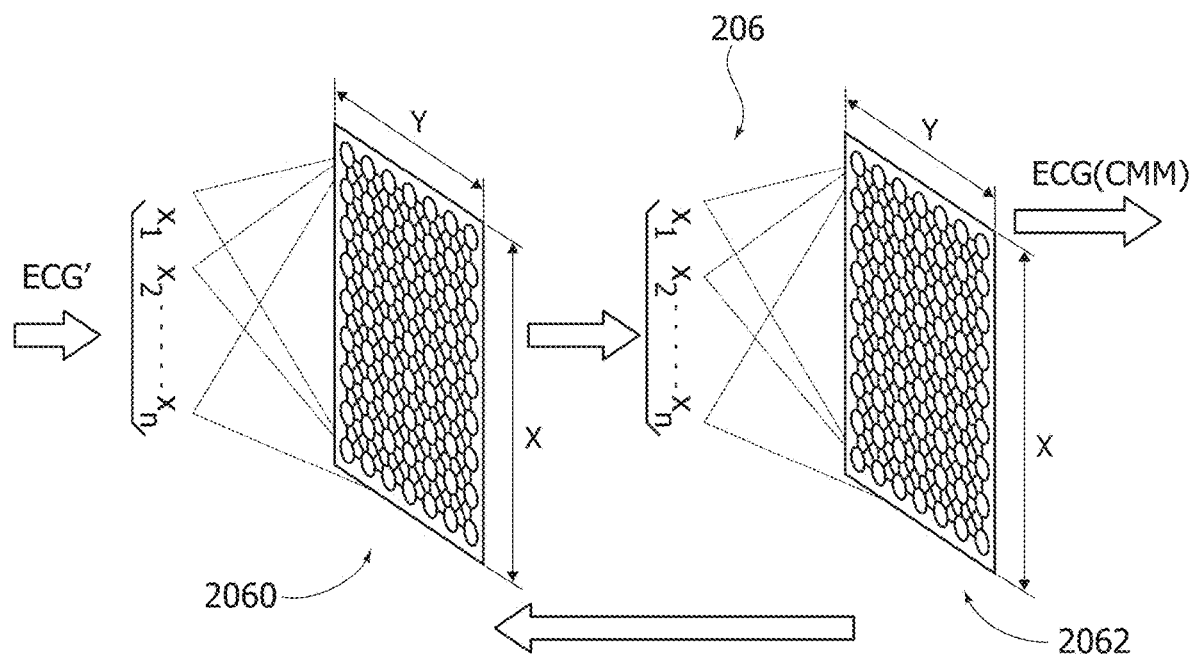

The diagram of FIG. 8 shows how the block 206 may complete learning of a non-linear model which makes it possible to map the input PPG pattern onto a corresponding ECG pattern.

For instance, in one or more embodiments, the signal ECG' reconstructed in the preceding LV neural block 204 can be input to the motor map block 206 which may include an input neural structure (e.g. lattice-like, for instance 8×8=64 neurons) 2060 and a corresponding output neural structure 2062 (e.g. lattice-like, for instance 8×8=64 neurons).

In one or more embodiments, the neural network used for the block 206 may be a modified version of a self-organizing map (SOM) Kohonen neural network with Winner-Take-All algorithm for updating weights w(x, y).

In one or more embodiments, also a random element $\mu(t)$ may be included which is able to improve the learning process.

For instance, the individual ECG patterns (that is ECG') reconstructed by the previous LV block 204 can be input to the input neurons of the motor map block 206. A self-organizing map (SOM) approach such as e.g. "Winner-Take-All" will activate the neuron that minimizes a distance (based on certain metrics, e.g. Euclidean) between its synaptic weights (win(t)) and the ECG pattern.

The activated (distance-minimizing) neuron will therefore activate the neurons in its neighborhood (defined e.g. by a classical Gaussian function $\beta(x,y,t)$) and the output layer of the neural network, that is, a corresponding output neuron and its relative neighborhood (again defined by $\beta(x,y,t)$). The synaptic weights of the output neuron which is activated can be denoted wout(x,y,t).

In one or more embodiments, the motor map block 206 will calculate a corrected ECG pattern $ECG^{CMM}(t+1)$ at time (t+1) from the ECG pattern ECG'(t) at time t as follows:

$$ECG^{CMM}(t+1) = ECG'(t) + \alpha(t) * \Sigma[\beta(x,y,t)(wout(t) + \mu(t))],$$

where $\alpha(t)$ represents the learning rate of network learning, while $\mu(t)$ represents a generalization component of the network randomly updated by means of a random value rand, e.g. as follows:

$$\mu(t+1) = \mu(t) + rand.$$

At each pattern ECG' presented, a corresponding $ECG^{CMM}$ will be calculated according to the formula above and compared with a corresponding "real" ECG pattern by computing an error metrics $E_{ave}$, for instance, squared or quadratic:

$$E_{ave}(t+1) = 1/N * \Sigma_j (ECG^{CMM}(t+1)_j - ECG^{target}(t+1)_j)^2$$

where N denotes the number of ECG patterns used in the training set and the index "j" identifies each individual ECG pattern.

The error $E_{ave}(t+1)$ at time (t+1) being found to be smaller than the previously calculated error $E_{ave}(t)$ at time t indicates that the system is learning "well" insofar as it is minimizing with a quadratic dynamics the average error between the reconstructed pattern $ECG^{CMM}(t+1)_j$ and the corresponding real one $ECG^{target}(t+1)_j$.

In the presence of a decrease in the average error as described above, indicating that the network is learning well, the activated neurons (both input and output) and the neurons included in their neighborhoods will be "rewarded" with a classic update:

$$win(t+1) = win(t) + \alpha(t) * \beta(x,y,t)[ECG'(t) - win(t)]$$

$$wout(t+1) = wout(t) + \alpha(t) * \beta(x,y,t)(ECG^{CMM}(t) - ECG^{target}(t)).$$

If, conversely the average error as described above is found to increase, which would indicate that the network is not learning well, the synaptic weights (win and wout) will not be updated, with only the random parameter $\mu(t)$ updated as described previously:

$$\mu(t+1) = \mu(t) + Rand.$$

In that way, the actual value space will be explored looking for a fix to reduce the error as described above.

The learning procedure as described can be continued until a desired accuracy is achieved.

In one more embodiments, a system 100 as exemplified herein may operate in two different modes.

In a first mode, the system will essentially perform a learning procedure, including acquisition of ECG samples via the ECG sensors 10 activated by the timing circuit 10a over a limited time span (e.g. not in excess of about 50 s., optionally about 40-50 s.) devoted to the system learning how to reconstruct ECG signals from PPG signals.

This mode, which notionally may be implemented even just once for good, may involve a driver D keeping both his or her hands over the sensors 10 e.g. on the steering wheel SW of the vehicle W.

Once such ECG sample acquisition completed (e.g. in 40-50 sec, possibly cumulatively over plural ECG sub-time-range sampling actions that overall add up to 40/50 sec) the ECG acquisition chain can be disabled (with an ensuing reduction of power absorption), with the system 100 entering a second operation as exemplified in FIG. 9.

In the second mode, an ECG signal—e.g. $ECG^{CMM}$ will be reconstructed from the PPG signals sensed at 12 (and possibly processed at 16 as discussed previously) and subjected to neural net processing as exemplified by the NSOS system 200.

The PPG signals in question can be detected at 12 as schematically represented in FIG. 9, namely even a single driver hand put on the steering wheel SW (or in the vicinity thereof, as facilitated by the optical sensing underlying PPG sensing).

Corresponding ECG signals may thus be reconstructed in the neural net processing system 200 to be supplied to an HRV estimation block to produce, e.g. from the R peak of the reconstructed ECG signal, an estimate of the HRV signal in turn adapted to produce a drowsiness signal. Both these acts are suited to be performed in a manner known per se: see e.g. the various documents cited in the introductory portion of the instant description.

Such a signal may be reflected e.g. by an alert A (e.g. sound and/or visual alert) to the drivers and/or control of the vehicle being taken over by an advanced driver-assistance systems (ADAS).

One or more embodiments may thus provide a simple and practical approach for detecting HRV from PPG signals sampled during driving.

In one or more embodiments, a method may include:

a) receiving (e.g. at 10, 14) over a limited (e.g. 10a) time duration sample ElectroCardioGraphy, ECG, signals indicative of heart pulsatile activity occurring with a variable heart rate, with receiving the sample ECG signals discontinued at the expiry of the limited time duration;

b) receiving (e.g. at 12, 16) PhotoPlethysmoGraphy, PPG, signals indicative of said heart pulsatile activity;

c) calculating (e.g. 200) a correlation between the sample ECG signals received over the limited (10a) time duration and the PPG signals received;

d) calculating reconstructed ECG signals (e.g. ECG', $ECG^{CMM}$) from the PPG signals received as a function of the correlation between the sample ECG signals received over the limited (10a) time duration and the PPG signals received; and e) estimating the heart rate variably, HRV, of the variable heart rate as a function of the reconstructed ECG signals.

In one or more embodiments, the limited time duration may include a cumulative duration (e.g. obtained either as a single ECG sampling time range or by summing plural ECG sampling sub-times) not in excess of about 50 seconds, preferably between about 40 seconds and 50 seconds.

In one or more embodiments, said calculating may include neural network processing of the sample ECG signals received over the limited time duration and the PPG signals received.

One or more embodiments, may include repeating over time at least the steps b), c) and d) of one or more embodiments, with neural network processing re-trained to take into account changes in the input dynamics of the PPG signals received.

In one or more embodiments, neural network processing may include calculating reconstructed ECG signals (e.g. ECG') as a function of the correlation between the sample ECG signals received over the limited time duration and the PPG signals received by multi-layer perceptron neural network processing (e.g. at 204), optionally Levenberg-Marquardt(LV) multi-layer perceptron neural network, LV MLP, processing.

In one or more embodiments, neural network processing may include applying to the ECG signals reconstructed via multi-layer perceptron neural network processing further motor map neural processing (e.g. 206) to provide improved reconstructed ECG signals (e.g. $ECG^{CMM}$), wherein heart rate variably, HRV, is estimated as a function of the improved reconstructed ECG signals.

One or more embodiments may include applying filtering and pattern recognition (e.g. at 14, 16) to the ECG signals received and the PPG signals received.

One or more embodiments may include calculating a drowsiness indicator (e.g. A) from the estimated heart rate variably, HRV.

One or more embodiments may be implemented on board a vehicle (e.g. V) driven by a driver (D) wherein the ECG and PPG signals received (10, 14, 12, 16) are indicative of the pulsatile activity of the heart of the vehicle driver (D) and the drowsiness indicator (A) estimated from heart rate variably, HRV, is indicative of the driver's drowsiness.

One or more embodiments may include, as a function of the drowsiness indicator estimated from heart rate variably, HRV, at least one of: issuing a drowsiness alert to the vehicle driver; and/or causing a driver assistance system to take over control of the vehicle.

In one or more embodiments, a system may include: ECG sensing circuitry configured for sensing over a limited time duration sample ECG signals indicative of heart pulsatile activity occurring with a variable heart rate, the ECG sensing circuitry configured to be disabled (10a) at the expiry of the limited time duration; PPG sensing circuitry configured for sensing PPG signals indicative of said heart pulsatile activity; neural network processing circuitry sensitive to the ECG signals sensed by the ECG sensing circuitry and to the PPG signals sensed by the PPG sensing circuitry and configured for: calculating a correlation between the sample ECG signals sensed over the limited time duration by the ECG sensing circuitry and the PPG signals sensed by the ECG sensing circuitry; calculating reconstructed ECG signals from the PPG signals sensed as a function of the correlation between the sample ECG signals sensed over the limited time duration and the PPG signals sensed; and the system configured for estimating the heart rate variably, HRV, of the variable heart rate as a function of the reconstructed ECG signals with the method of one or more embodiments.

One or more embodiments, may be installed on board a vehicle for driving by a driver wherein the ECG and PPG signals sensed are indicative of the pulsatile activity of the heart of the vehicle driver and the drowsiness indicator (A) estimated from heart rate variably, HRV, is indicative of the driver's drowsiness.

One or more embodiments may include a drowsiness alert indicator activatable as a function of the drowsiness indicator estimated from heart rate variability.

In one or more embodiments, a vehicle may be equipped with a system according to one or more embodiments and a driver assistance system to take over control of the vehicle as a function of the drowsiness indicator estimated from heart rate variability.

In one or more embodiments, a computer program product loadable in the memory of at least one processing circuit (e.g. 200) may include software code portions for executing the steps of the method of one or more embodiments when the product is run on at least one processing circuit.

Without prejudice to the underlying principles, the details and embodiments may vary, even significantly, with respect to what has been described by way of example only, without departing from the extent of protection.

What is claimed is:

1. A method, comprising:
   receiving, over a limited time duration, sample electrocardiography (ECG) signals indicative of heart pulsatile activity occurring with a variable heart rate, wherein receiving the sample ECG signals is discontinued at an expiry of the limited time duration;
   receiving photoplethysmography (PPG) signals indicative of the heart pulsatile activity;
   determining a correlation between the sample ECG signals and the PPG signals;
   determining reconstructed ECG signals for times occurring after the expiry of the limited time duration from the PPG signals as a function of the correlation between the sample ECG signals and the PPG signals; and estimating a heart rate variability of the variable heart rate as a function of the reconstructed ECG signals.

2. The method of claim 1, wherein the limited time duration comprises a cumulative duration less than or equal to about 50 seconds.

3. The method of claim 2, wherein the cumulative duration is between about 40 seconds and 50 seconds.

4. The method of claim 1, wherein determining the correlation and determining the reconstructed ECG signal comprise neural network processing of the sample ECG signals and the PPG signals.

5. The method of claim 4, further comprising repeating, over time, at least receiving the PPG signals, determining the correlation, and determining the reconstructed ECG signals with the neural network processing re-trained to take into account changes in input dynamics of the PPG signals.

6. The method of claim 4, wherein the neural network processing comprises determining reconstructed ECG signals from the PPG signals as a function of the correlation between the sample ECG signals by multi-layer perceptron neural network processing.

7. The method of claim 6, wherein the multi-layer perceptron neural network processing comprises Levenberg-Marquardt multi-layer perceptron neural network processing.

8. The method of claim 7, wherein the neural network processing comprises applying to the reconstructed ECG signals reconstructed via the multi-layer perceptron neural network processing, a further motor map neural processing to provide further reconstructed ECG signals, wherein the heart rate variability is estimated as a function of the further reconstructed ECG signals.

9. The method of claim 1, further comprising applying filtering and pattern recognition to the sample ECG signals and the PPG signals.

10. The method of claim 1, further comprising determining a drowsiness indicator from the heart rate variability.

11. The method of claim 10, wherein the sample ECG signals and the PPG signals are indicative of the pulsatile activity of a heart of a driver of a vehicle, and wherein the drowsiness indicator is indicative of the driver's drowsiness.

12. The method of claim 11, further comprising, as a function of the drowsiness indicator estimated from the heart rate variability, issuing a drowsiness alert to the driver, causing a driver assistance system to take over control of the vehicle, or both.

13. A system, comprising:
an ECG sensing circuitry configured to sense, over a limited time duration, sample ECG signals indicative of heart pulsatile activity occurring with a variable heart rate, wherein the ECG sensing circuitry is configured to be disabled at an expiry of the limited time duration;
a PPG sensing circuitry configured to sense PPG signals indicative of the heart pulsatile activity; and
a neural network processing circuitry sensitive to the sample ECG signals sensed by the ECG sensing circuitry and to the PPG signals sensed by the PPG sensing circuitry, wherein the neural network processing circuitry is configured to:
determine a correlation between the sample ECG signals and the PPG signals;
determine reconstructed ECG signals for times occurring after the expiry of the limited time duration from the PPG signals as a function of the correlation between the sample ECG signals and the PPG signals; and
estimate a heart rate variability of the variable heart rate as a function of the reconstructed ECG signals.

14. The system of claim 13, wherein the system is comprised in a vehicle for driving by a driver, wherein the sample ECG signals and the PPG signals are indicative of pulsatile activity of a heart of the driver.

15. The system of claim 14, wherein the neural network processing circuitry is further configured to determine a drowsiness indicator estimated from the heart rate variability, the drowsiness indicator being indicative of the driver's drowsiness.

16. The system of claim 15, comprising a drowsiness alert indicator activatable as a function of the drowsiness indicator estimated from the heart rate variability.

17. A vehicle, comprising:
a system for processing electrophysiological signals, the system comprising:
an ECG sensing circuitry configured to sense, over a limited time duration, sample ECG signals indicative of heart pulsatile activity occurring with a variable heart rate, wherein the ECG sensing circuitry is configured to be disabled at an expiry of the limited time duration;
a PPG sensing circuitry configured to sense PPG signals indicative of the heart pulsatile activity; and
a neural network processing circuitry sensitive to the sample ECG signals sensed by the ECG sensing circuitry and to the PPG signals sensed by the PPG sensing circuitry, wherein the neural network processing circuitry is configured to:
determine a correlation between the sample ECG signals and the PPG signals;
determine reconstructed ECG signals for times occurring after the expiry of the limited time duration from the PPG signals as a function of the correlation between the sample ECG signals and the PPG signals;
estimate a heart rate variability of the variable heart rate as a function of the reconstructed ECG signals; and
determine a drowsiness indicator estimated from the heart rate variability, the drowsiness indicator being indicative of a driver's drowsiness; and
a driver assistance system configured to take over control of the vehicle as a function of the drowsiness indicator.

18. The vehicle of claim 17, wherein the limited time duration comprises a cumulative duration less than or equal to about 50 seconds.

19. The vehicle of claim 17, wherein the neural network processing circuitry is configured to determine the reconstructed ECG signals from the PPG signals as the function of the correlation between the sample ECG signals by multi-layer perceptron neural network processing.

20. A device, comprising:
a processor; and
a non-transitory computer-readable storage medium storing a computer program product to be executed by the processor, the computer program product including instructions for:
receiving, over a limited time duration, sample electrocardiography (ECG) signals indicative of heart pulsatile activity occurring with a variable heart rate, wherein receiving the sample ECG signals is discontinued at an expiry of the limited time duration;
receiving photoplethysmography (PPG) signals indicative of the heart pulsatile activity;

determining a correlation between the sample ECG signals and the PPG signals;

determining reconstructed ECG signals for times occurring after the expiry of the limited time duration from the PPG signals as a function of the correlation between the sample ECG signals and the PPG signals; and estimating a heart rate variability of the variable heart rate as a function of the reconstructed ECG signals.

\* \* \* \* \*